United States Patent
Yang et al.

(10) Patent No.: US 10,942,233 B2
(45) Date of Patent: Mar. 9, 2021

(54) MULTI-TURN MAGNETIC RESONANCE IMAGING (MRI) ARRAY COIL WITH RING DECOUPLING FOR IMPROVED COIL ISOLATION

(71) Applicant: Quality Electrodynamics, LLC, Mayfield Village, OH (US)

(72) Inventors: Xiaoyu Yang, Indiana, PA (US); Haoqin Zhu, Mayfield Village, OH (US); Tsinghua Zheng, Chesterland, OH (US)

(73) Assignee: Quality Electrodynamics, LLC, Mayfield Village, OH (US)

( * ) Notice: Subject to any disclaimer, the term of this patent is extended or adjusted under 35 U.S.C. 154(b) by 0 days.

(21) Appl. No.: 16/266,346

(22) Filed: Feb. 4, 2019

(65) Prior Publication Data

US 2019/0257897 A1    Aug. 22, 2019

Related U.S. Application Data

(60) Provisional application No. 62/632,266, filed on Feb. 19, 2018.

(51) Int. Cl.
    *G01R 33/36*    (2006.01)
    *G01R 33/34*    (2006.01)
    *A61B 5/055*    (2006.01)

(52) U.S. Cl.
    CPC ............ *G01R 33/365* (2013.01); *A61B 5/055* (2013.01); *G01R 33/34084* (2013.01); *G01R 33/34046* (2013.01)

(58) Field of Classification Search
    CPC .............. A61B 5/055; G01R 33/34046; G01R 33/34084; G01R 33/365; G01R 33/34076; G01R 33/3453
    See application file for complete search history.

(56) References Cited

U.S. PATENT DOCUMENTS

| 7,091,721 B2 | 8/2006 | Jevtic | |
| 2002/0169374 A1* | 11/2002 | Jevtic | G01R 33/3415 600/422 |

(Continued)

OTHER PUBLICATIONS

Borsboom, Henny M., et al. "Low-frequency quadrature mode birdcage resonator." Magnetic Resonance Materials in Physics, Biology and Medicine 5.1 (1997): 33-37. (Year: 1997).*

(Continued)

*Primary Examiner* — Rishi R Patel
(74) *Attorney, Agent, or Firm* — Eschweiler & Potashnik, LLC (57) ABSTRACT

Embodiments relate to multi-turn magnetic resonance imaging (MRI) radio frequency (RF) coil arrays employing ring decoupling, and MRI apparatuses employing such coil arrays. One example embodiment comprises: four or more RF coil elements that enclose a cylindrical axis, wherein each RF coil element comprises a first capacitor of that RF coil element and a loop comprising at least two turns; and a ring structure that facilitates decoupling of the RF coil elements, wherein each RF coil element is adjacent to two neighboring RF coil elements and is non-adjacent to one or more other coil elements, wherein each RF coil element has a shared side in common with the ring structure, wherein the shared side comprises a second capacitor of that RF coil element with a capacitance selected to mitigate inductive coupling between that RF coil element and non-adjacent RF coil elements.

17 Claims, 5 Drawing Sheets

(56) References Cited

U.S. PATENT DOCUMENTS

| | | | |
|---|---|---|---|
| 2005/0253582 A1* | 11/2005 | Giaquinto | G01R 33/3415 324/318 |
| 2014/0152309 A1* | 6/2014 | Kozlov | G01R 33/5612 324/314 |
| 2014/0300355 A1* | 10/2014 | Fautz | G01R 33/28 324/309 |

OTHER PUBLICATIONS

Li, Ye, et al. "ICE decoupling technique for RF coil array designs." Medical physics 38.7 (2011): 4086-4093. (Year: 2011).*

\* cited by examiner

MULTI-TURN MAGNETIC RESONANCE IMAGING (MRI) ARRAY COIL WITH RING DECOUPLING FOR IMPROVED COIL ISOLATION

REFERENCE TO RELATED APPLICATIONS

This application claims the benefit of U.S. Provisional Patent Applications No. 62/632,266 filed Feb. 19, 2018, entitled "MULTI-TURN MAGNETIC RESONANCE IMAGING (MRI) ARRAY COIL WITH RING DECOUPLING FOR IMPROVED COIL ISOLATION", the contents of which are herein incorporated by reference in their entirety.

BACKGROUND

Magnetic resonance imaging (MRI) involves the transmission and receipt of radio frequency (RF) energy. RF energy may be transmitted by a coil. Resulting magnetic resonance (MR) signals may also be received by a coil. In early MRI, RF energy may have been transmitted from a single coil and resulting MR signals received by a single coil. Later, multiple receivers may have been used in parallel acquisition techniques. Similarly, multiple transmitters may have been used in parallel transmission (pTx) techniques.

RF coils create the $B_1$ field that rotates the net magnetization in a pulse sequence. RF coils may also detect precessing transverse magnetization. Thus, RF coils may be transmit (Tx) coils, receive (Rx) coils, or transmit and receive (Tx/Rx) coils. An imaging coil should be able to resonate at a selected Larmor frequency. Imaging coils include inductive elements and capacitive elements. The inductive elements and capacitive elements have been implemented according to existing approaches using two terminal passive components (e.g., capacitors). The resonant frequency, f, of an RF coil is determined by the inductance (L) and capacitance (C) of the inductor capacitor circuit according to equation (1):

$$f = \frac{1}{2\pi\sqrt{LC}} \quad (1)$$

Imaging coils may need to be tuned. Tuning an imaging coil may include varying the value of a capacitor. Recall that frequency: $f=\omega/(2\pi)$, wavelength in vacuum: $\Delta=c/f$, and $\Delta=4.7$ m at 1.5 T. Recall also that the Larmor frequency: $f_0=\gamma B_0/(2\pi)$, where (for $^1$H nuclei) $\gamma/(2\pi)=42.58$ MHz/T; at 1.5 T, $f_0=63.87$ MHz; at 3 T, $f_0=127.73$ MHz; at 7 T, $f_0=298.06$ MHz. Basic circuit design principles include the fact that capacitors add in parallel (impedance $1/(jC\omega)$) and inductors add in series (impedance $jL\omega$).

In existing systems, when MRI coils that are tuned to the same radio frequency are positioned close together, which may occur, for example, in phased array coils, the MRI coils may inductively couple to each other, which causes the MRI coils to detune each other. Detuning due to inductive coupling reduces image quality as compared to using single coils individually. Existing phased array coils may address the detuning due to inductive coupling problem by overlapping coils or by using preamplifiers that dampen current flow in individual coils.

DETAILED DESCRIPTION

The present disclosure will now be described with reference to the attached drawing figures, wherein like reference numerals are used to refer to like elements throughout, and wherein the illustrated structures and devices are not necessarily drawn to scale.

Various embodiments discussed herein comprise multi-turn MRI (Magnetic Resonance Imaging) coils (and methods of employing such coils and/or multiple-coil system), which are employable in a MRI system having reduced coupling (inductive and/or capacitive) between channels. Embodiments discussed herein can comprise multi-turn coil element(s) that employ ring decoupling for improved coil isolation. In various aspects, embodiments discussed herein include coil arrays comprising multi-turn coils using ring decoupling as discussed herein, and/or MRI systems comprising such coil arrays.

Figure 1:
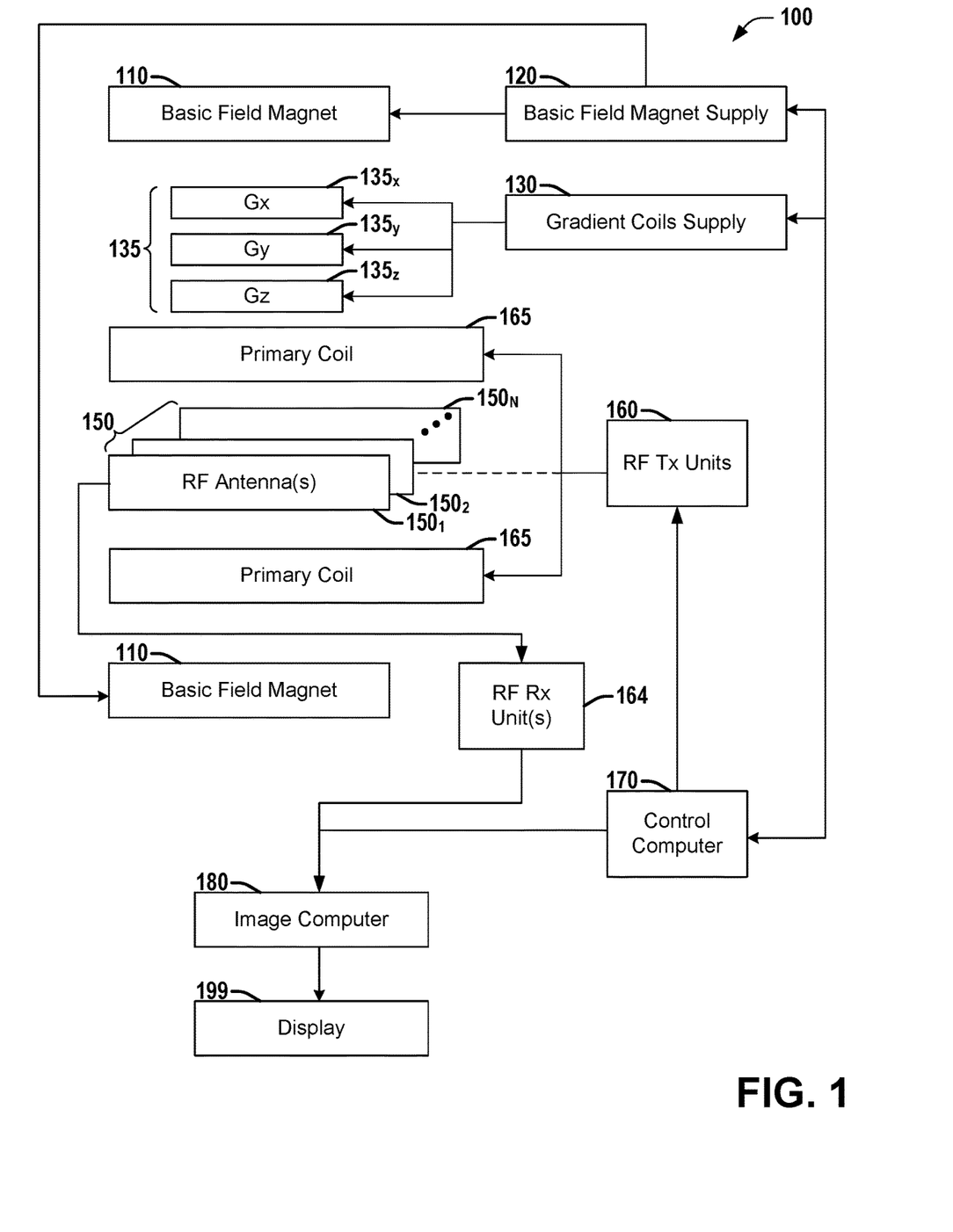
FIG. 1 is a block diagram illustrating an example MRI apparatus that can be configured with example MRI RF coils, coil elements, coil arrays, or circuitry according to one or more embodiments described herein.

Embodiments described herein can be implemented in a MRI (Magnetic Resonance Imaging) system using any suitably configured hardware and/or software. Referring to FIG. 1, illustrated is an example MRI apparatus 100 that can be configured with example MRI RF coils, coil elements, coil arrays, or circuitry according to one or more embodiments described herein. Apparatus 100 includes basic field magnet(s) 110 and a basic field magnet supply 120. Ideally, the basic field magnets 110 would produce a uniform $B_0$ field. However, in practice, the $B_0$ field may not be uniform, and may vary over an object being imaged by the MRI apparatus 100. MRI apparatus 100 can include gradient coils 135 configured to emit gradient magnetic fields like $G_x$ (e.g., via an associated gradient coil $135_x$), $G_y$ (e.g., via an associated gradient coil $135_y$) and $G_z$ (e.g., via an associated gradient coil $135_z$). The gradient coils 135 can be controlled, at least in part, by a gradient coils supply 130. In some examples, the timing, strength, and orientation of the gradient magnetic fields can be controlled, and thus selectively adapted during an MRI procedure.

MRI apparatus 100 can include a primary coil 165 configured to generate RF pulses. The primary coil 165 can be a whole body coil. The primary coil 165 can be, for example, a birdcage coil. The primary coil 165 can be controlled, at least in part, by an RF transmission unit 160. RF transmission unit 160 can provide a signal to primary coil 165.

MRI apparatus 100 can include a set of RF antennas 150 (e.g., one or more RF antennas $150_1$-$150_N$, which can be as described herein). RF antennas 150 can be configured to generate RF pulses and to receive resulting magnetic resonance signals from an object to which the RF pulses are directed. In some embodiments, RF antennas 150 can be configured to inductively couple with primary coil 165 and generate RF pulses and to receive resulting magnetic resonance signals from an object to which the RF pulses are directed. In other embodiments, RF antennas 150 can be electrically coupled to a power source (e.g., RF Tx unit 160) that can drive RF antennas 150 to generate RF pulses, and RF antennas can also be configured to receive resulting magnetic resonance signals from an object to which the RF pulses are directed. In one embodiment, one or more members of the set of RF antennas 150 can be fabricated from flexible coaxial cable, or other conductive material. The set of RF antennas 150 can be connected with an RF receive unit 164.

The gradient coils supply 130 and the RF transmission units 160 can be controlled, at least in part, by a control computer 170. The magnetic resonance signals received from the set of RF antennas 150 can be employed to generate an image, and thus can be subject to a transformation process like a two dimensional fast Fourier transform (FFT) that generates pixilated image data. The transformation can be performed by an image computer 180 or other similar processing device. The image data can then be shown on a display 199. RF Rx Units 164 can be connected with control computer 170 or image computer 180. While FIG. 1 illustrates an example MRI apparatus 100 that includes various components connected in various ways, it is to be appreciated that other MRI apparatus can include other components connected in other ways, and can be employed in connection with various embodiments discussed herein.

In one embodiment, MRI apparatus 100 includes control computer 170. In one example, a member of the set of RF antennas 150 can be individually controllable by the control computer 170. A member of the set of RF antennas 150 can be an example MRI RF coil array including, for example, MRI RF coil arrays as described herein. In various embodiments, the set of RF antennas 150 can include various combinations of example embodiments of MRI RF coil arrays, elements or example embodiments of MRF RF coil arrays, including single-layer MRI RF coil elements or single-layer MRI RF coil arrays, according to various embodiments described herein.

An MRI apparatus can include, among other components, a controller (e.g., control computer 170) and an RF coil (e.g., primary coil 165) operably connected to the controller. The controller can provide the RF coil with a current, a voltage, or a control signal. The coil can be a whole body coil. The coil can inductively couple with an example MRI RF coil element, or MRI RF coil array, as described herein. Control computer 170 can provide a DC bias current, or control a DC bias control circuit to control the application of a DC bias current to MRI RF coil arrays or elements that can be part of antennas 150.

Figure 2:
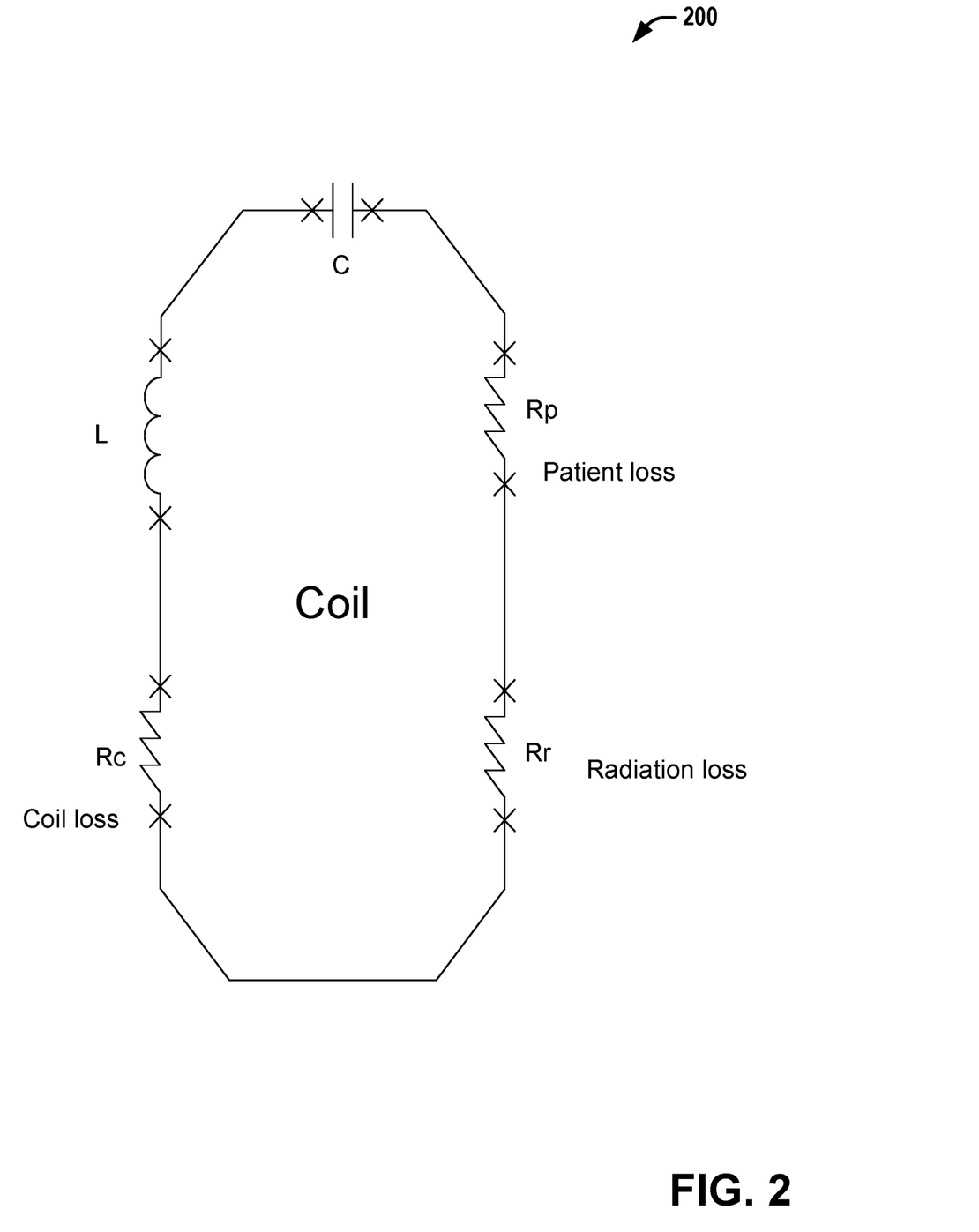
FIG. 2 is a diagram illustrating a typical RF coil element showing different losses, which can be employed in connection with various aspects discussed herein.

A MRI RF coil is a resonant circuit. Referring to FIG. 2, illustrated is a diagram of a typical RF coil element 200 showing different losses, which can be employed in connection with various aspects discussed herein. RF coil element 200 has one or more inductors with equivalent inductance L and one or more capacitors with equivalent capacitance C. Normally the capacitor(s) used is a very high Q capacitor, which can be considered essentially lossless. The inductor is the (e.g., copper) trace of the coil and has its own resistive loss, referred to herein as coil loss or Rc. When the RF current flows in the coil, the current establishes an alternating magnetic field $B_1$ around the coil. From Maxwell's equations, it can be seen that an alternating magnetic field generates an alternating electrical field. Thus, this alternating magnetic field $B_1$ will generate a RF signal that can be transmitted far away. This is referred to herein as radiation loss or Rr. If a lossy conductive material, such as human anatomy, which includes conductive body fluid and muscle, is exposed to the established magnetic field $B_1$, then small eddy current flows will be induced in the conductive material, causing energy loss. This energy loss is referred to herein as patient loss or Rp. Therefore, there are three major energy losses for a RF coil: coil loss, radiation loss, and patient loss. From RF theory, it can be shown that radiation loss and patient loss are dominant at high RF frequency, such as associated with a $B_0$ field strength of 3 T and higher. Coil loss, on the other hand, is dominant at low frequency, such as associated with a $B_0$ field strength of <1 T.

As discussed above, at low field, coil loss is dominant. As an example, a one-turn coil can be considered. At the resonant frequency ($\omega_0$), the coil Q can be written as in equation (1):

$$Q = \frac{\omega_0 L}{R_c} \quad (1)$$

If the coil is wound with N turns instead of one turn, then $L \sim N^2$ and $Rc \sim N$.

From the scaling of L and Rc based on N, along with equation (1), it can be seen that $Q \sim N$. Q is very important, because Q has a significant impact on coil SNR (Signal-to-Noise Ratio) and/or image quality. What this means is that coil Q increases with more coil turns. Of course, when the number of turns increases, the magnetic field $B_1$ is stronger with the same current flowing in the coil. As a result, the radiation loss increases with stronger $B_1$ or more turns. As such, the relationship between Q and N is not really a linear proportional relation. Regardless, it is advantageous to use multi-turn coil as coil element at low frequency to achieve higher coil Q and SNR. An additional consideration is the unloaded coil Q vs loaded coil Q ratio impact from the multi-turn coil, because it is fundamentally linked to the coil SNR. Since the established magnetic field $B_1$ is proportional to N for the same current flow, the induced eddy current voltage will be proportional to N, thus the patient loss power is $\sim N^2$. Because the coil loss is proportional to Rc (which is proportional to N), then the Unloaded Q/loaded coil Q ratio becomes larger for more turns, which is also good for coil SNR.

For a multiple-channel array coil, one or more of overlap, transformers, or capacitors can be employed to decouple and/or isolate the different coil elements. The SNR impact from coil elements isolation differs with respect to patient noise and coil noise. For patient noise, even good coil isolation has no impact to SNR because the patient noise is from the same source, the patient. For different coil elements, the patient noise from the same source (the patient) is correlated regardless of the coil isolation. However, coil noise is a different story. Each coil has its own copper-coil loss. All coil losses are independent from each other, meaning they are non-correlated. If the coil elements do not have good isolation between them, then noise from one element will leak into a second element to make the noise in that second coil element higher. As a result, SNR decreases. Thus, good element isolation has a significant impact on SNR at low field.

Head, knee, leg, and wrist are common anatomies for MRI. Each of these anatomies shares a similar cylindrical former shape. If a multi-channel array coil is built around a cylinder, the directly neighboring elements are easy to decouple by using overlap. For non-directly neighboring elements, decoupling can be achieved via a transformer or capacitor approach. However, either of these approaches will introduce non-image contributed copper loss from connecting the transformer or capacitor, which decreases SNR. Some existing systems employ one method to decouple coil elements on a cylindrical shape for non-overlapping coil elements that can be employed for single-turn coil elements. In various aspects discussed herein, embodiments can employ a ring structure to decouple non-neighboring elements, and can use overlap to decouple/capacitor to decouple neighboring elements for multi-turn coil elements at low field.

Figure 3:
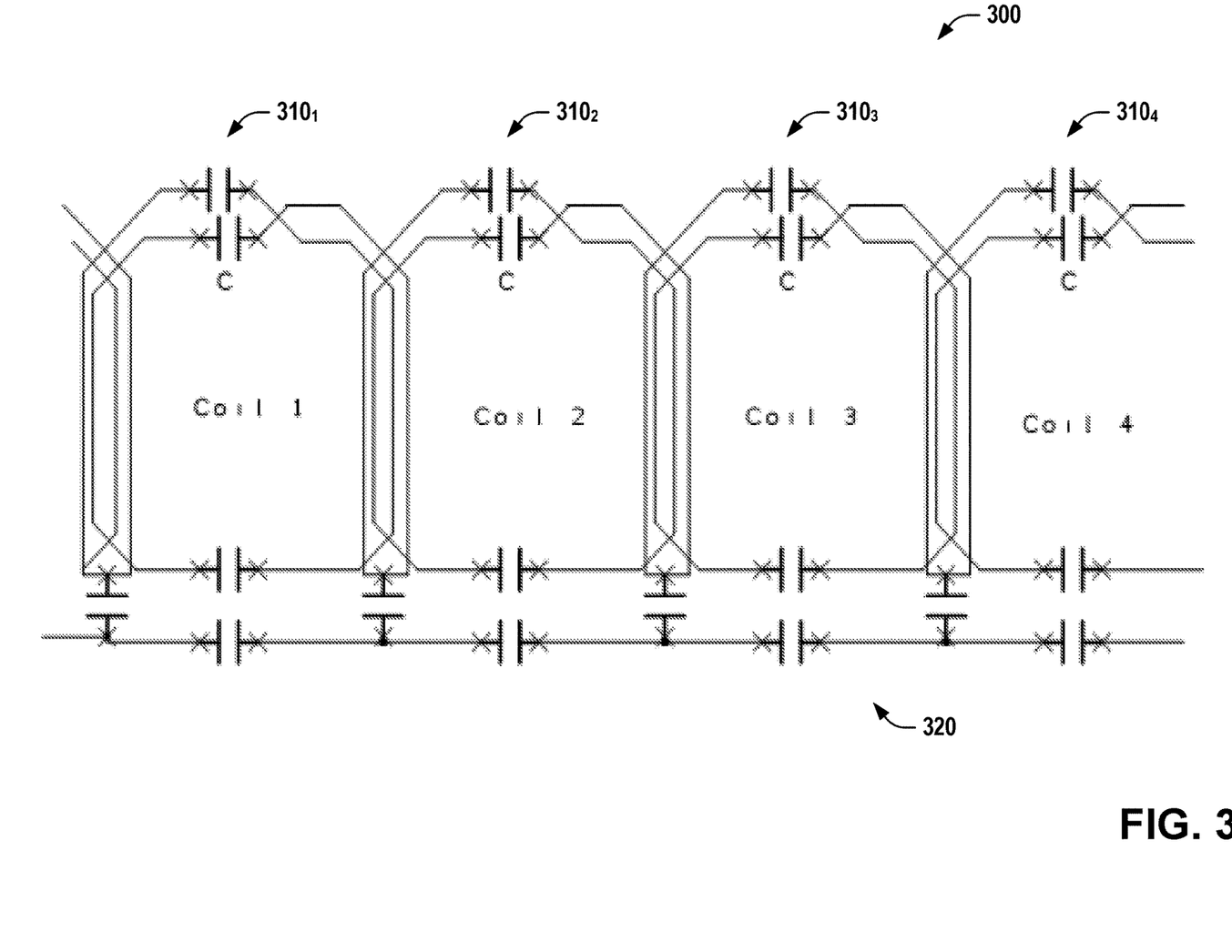
FIG. 3 is a diagram illustrating an example embodiment of the structure of a 4-coil element two-turn array coil useable around a cylindrical former, according to various aspects discussed herein.

Aspects of various embodiments can be better understood in connection with an example embodiment. Referring to FIG. 3, illustrated is a diagram of an example embodiment of the structure of a 4-coil element ($310_1$-$310_4$) two-turn array coil 300 useable around a cylindrical former, according to various aspects discussed herein. In various embodiments, coil elements of coil 300 can be symmetrically aligned around and circumferentially enclose a cylindrical axis of the cylindrical former (e.g., enclose via spanning the entire circumference of a cylindrical volume comprising the cylindrical former). Each coil element ($310_1$-$310_4$) can share at least one side with at least one ring structure (e.g., ring 320, which can be a closed circuit path that comprises a shared portion with each of the coil elements $310_1$-$310_4$) that can facilitate decoupling of coil elements as discussed herein.

Figure 4:
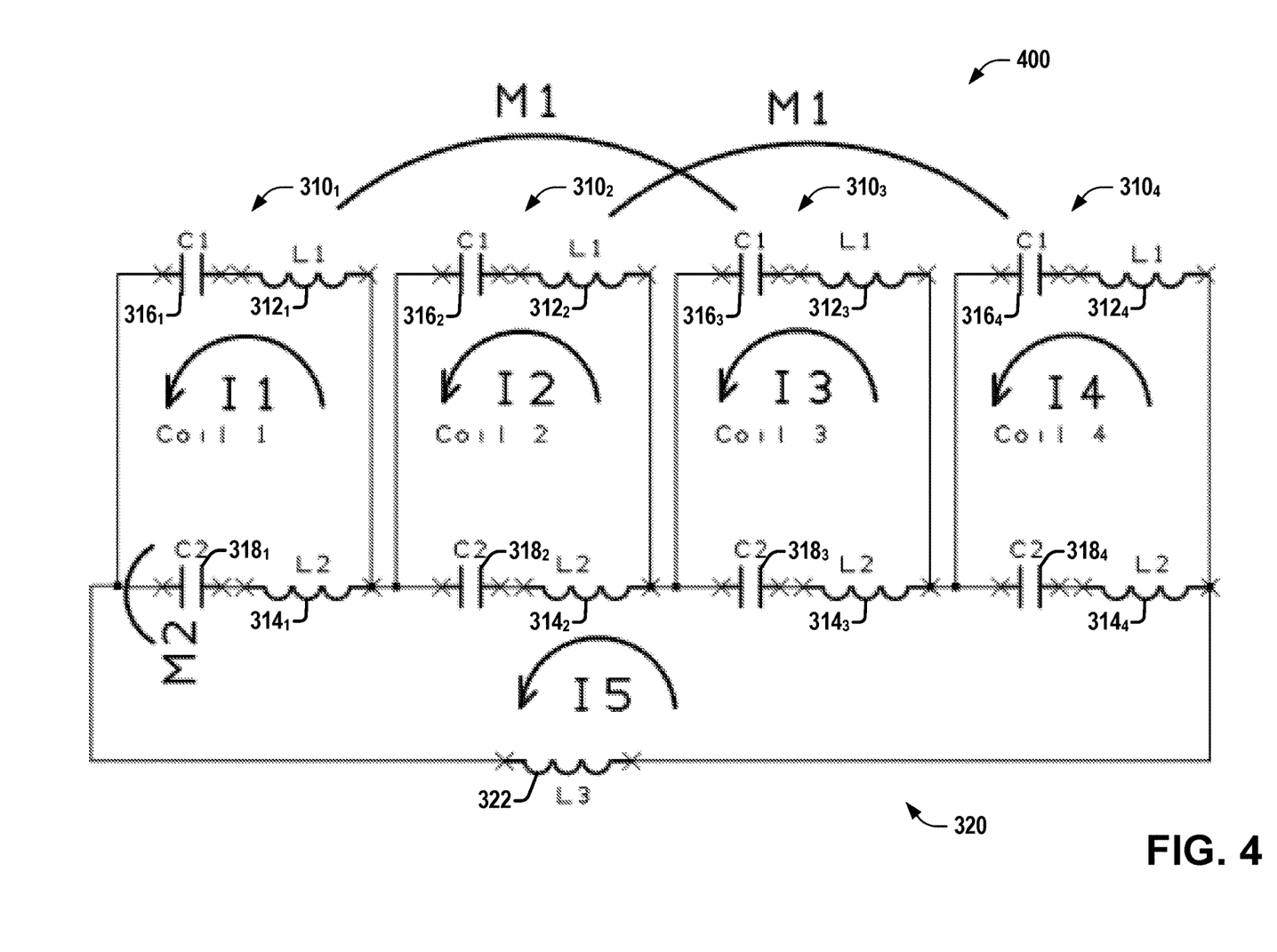
FIG. 4 is a diagram illustrating the equivalent circuit diagram of the coil array of FIG. 3.

Referring to FIG. 4, illustrated is a circuit diagram 400 that is the equivalent circuit diagram of coil array 300 of FIG. 3. To simplify the analysis of coil array 300, the following conditions can be assumed in analyzing FIG. 4: (1) The cylinder is perfectly round, such that many symmetry simplifications apply; (2) Each coil $310_i$ is identical to the others with respect to size, inductance, capacitance, etc.; (3) As a result, each coil inductance and capacitance can be split as L1 ($312_i$), L2 ($314_i$, on a side shared with ring 320), C1 ($316_i$) and C2 ($318_i$, on the side shared with ring 320); (4) Overlap/capacitor decoupling can be used to decouple directly neighboring coils, and as a result, significant mutual inductance only exists between coils 1 ($310_1$) and 3 ($310_3$) and coils 2 ($310_2$) and 4 ($310_4$), which is defined as M1 using symmetry; (5) There is mutual inductance between coils 1 to 4 ($310_1$-$310_4$) and the ring coil (I5), which is referred to as M2 (because M2 is not important for clarifying the decoupling techniques discussed here, it is set to be M2=0 in the following discussion); (6) In each coil $310_i$, C1 ($316_i$) is mainly for frequency tuning of that coil element, and C2 ($318_i$) is for isolation adjustment, while L1 ($312_i$) and L2 ($314_i$) are fixed copper traces and not adjustable; (7) L3 (322) is the self-inductance that cannot be included by all L2s ($314_i$) for the ring, which is mainly determined by the covered area of the ring (If the area is minimized, e.g., via creating a ring return path very close to the copper for eliminating the large cylindrical former ring shape, then L3 (322) can be very small or near zero); and (8) Coil loss is ignored.

Using Kirchhoff's Law, equation (2) can be determined as follows:

$$\begin{cases} I_1*(Z_1+Z_2)+0+j\omega M_1 I_3+0-I_5*Z_2=0 \\ 0+I_2*(Z_1+Z_2)+0+j\omega M_1 I_4-I_5*Z_2=0 \\ \quad \ldots \\ I_1*Z_2+I_2*Z_2+I_3*Z_2+I_4*Z_2-I_5*(4Z_2+Z_3)=0 \end{cases} \quad (2)$$

Where $Z_1=j(\omega L_1-1/\omega C_1)$, $Z_2=j(\omega L_2-1/\omega C_2)$ and $Z_3=\omega L_3$ (wherein the equations for coils 3 and 4 are similar to those for coils 1 and 2, including a $I_m*(Z_1+Z_2)$ term for m=3 or 4 and a $j\omega M_1 I_n$ for n=m−2 (1 or 2)).

To obtain the intended isolation, consider a scenario wherein signal is injected into $I_1$ but not $I_2$, $I_3$, $I_4$, or $I_5$. Clearly, $I_2=I_3=I_4=0$ due to the isolation condition, but $I_5$ may not be 0. Additionally, as $L_3$ can be minimized, as discussed above, $L_3=0$ in this analysis. Then the 5 equations of equation (2) above can be simplified as in equation (3):

$$\begin{cases} I_1(Z_1+Z_2)-I_5 Z_2=0 \\ j\omega M_1 I_1 - I_5 * Z_2 = 0 \\ I_1 Z_2 - I_5(4Z_2)=0 \end{cases} \quad (3)$$

Solving equation (3) gives $Z_2=4j\omega M_1$ and $Z_1=-3j\omega M_1$. This condition will ensure good isolation between coils 1 and 3 and between coils 2 and 4. Under this condition, the same resonant frequency can be derived for each loop except $I_5$. From this, a relationship between the resonant frequency $\omega_0$, inductance L, capacitance C, and mutual inductance M ($M_1$) can be determined, as in equation (4):

$$\omega_0 = \frac{1}{\sqrt{(L-M)C}} \quad (4)$$

Where L is the sum of $L_1$ and $L_2$ and C is the equivalent capacitance of $C_1$ and $C_7$ in series $$\left(\frac{1}{C}=\frac{1}{C_1}+\frac{1}{C_2}\right).$$

From equation (4), a value of $C_1$ can be determined (e.g., $$C_1 = \frac{C_2}{C_2 \omega_0^2 (L-M)-1}$$

for the example embodiment of FIGS. 3 and 4), and can be employed in various embodiments to reduce and/or eliminate coupling from non-adjacent coil elements (e.g., by selecting a value of $C_2$ that compensates M.

Although the example embodiment shown in FIGS. 3 and 4 has four multi-turn coil elements (or loops) around a cylinder, the same analysis can be applied for arrays with five or more multi-turn coil elements around the cylinder (for three or fewer, there are no non-adjacent coil elements). Additionally, although a 4 or 5-loop coil embodiment can obtain complete decoupling among coil elements via techniques discussed herein, an array of 6, 7 or more coil elements cannot. However, reasonably good isolation can still be obtained for arrays of 6, 7 or 8 coil elements (and some isolation for a greater number of coil elements) using techniques discussed herein, they cannot be decoupled completely. As a practical matter, the amount of decoupling provided via techniques discussed herein is sufficient at least for up to 8 coil elements, and possibly more, depending on embodiments and application.

Example MRI RF coil elements, MRI RF coil arrays, MRI RF coils, apparatuses, and other embodiments, can be configured, for example, as bird cage coils. Although FIGS. 3 and 4 illustrate a single row of multi-turn coil elements that can be cylindrically arranged about an axis, various embodiments can comprise one or more rows of multi-turn RF coil elements cylindrically arranged about an axis (and longitudinally offset from each other), wherein each row can be as described herein (e.g., in connection with FIGS. 3-4). Coupling between coil elements of different such rows is small.

Figure 5:
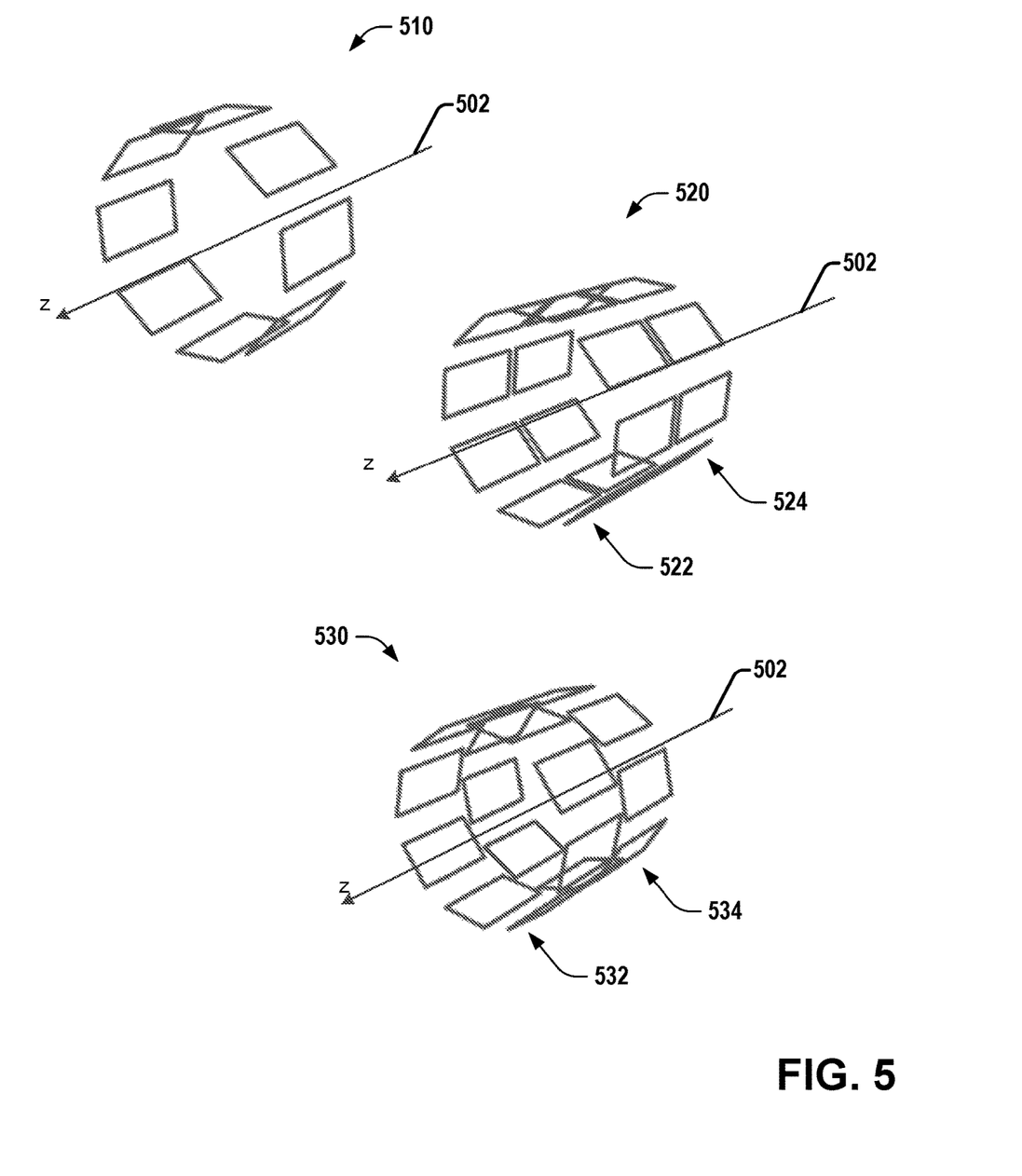
FIG. 5 is a diagram illustrating various embodiments of multi-turn coil arrays that can be employed in various aspects discussed herein.

Referring to FIG. 5, illustrated is a diagram showing various embodiments of multi-turn coil arrays that can be employed in various aspects discussed herein. Multi-turn MRI RF coil array 510 is one example embodiment that comprises at least four multi-turn MRI RF coil elements (although FIG. 5 shows eight coil elements, in various embodiments, four or more can be employed) arranged in a single-row configuration. Each of the at least four multi-turn MRI RF coil elements can comprise two or more turns, and can be as described above, for example, in connection with FIGS. 3-4. FIG. 5 also illustrates another example embodiment of a multi-turn MRI RF coil array 520 that includes multi-turn MRI RF coil elements arranged in a two-row configuration. Multi-turn MRI RF coil array 520 includes a first row 522 longitudinally offset from and rotationally (e.g., azimuthally) aligned with a second row 524. First row 522 includes at least four RF coil elements (e.g., up to eight). Second row 524 includes at least four RF coil elements (e.g., up to eight). FIG. 5 further illustrates an additional multi-turn MRI RF coil array 530. Multi-turn MRI coil array 530 is similar to multi-turn MRI RF coil array 520, except the first row 532 is not aligned with second row 534. For example, first row 532 may be rotated a number of degrees around a central axis (e.g., z axis) shared with second row 534, while 534 is not rotated, or is rotated a different number of degrees. In different embodiments, first row 532 may be aligned to within a threshold level of alignment with second row 534. In one embodiment, MRI RF coil array 520 includes a first plurality of RF coil elements (e.g., first row 522) and a second plurality of RF coil elements (e.g., second row 524). The first plurality of RF coil elements and the second plurality of RF coil elements are radially disposed about a longitudinal axis 502. The first plurality and the second plurality may be longitudinally offset a threshold distance greater than zero along the longitudinal axis 502. In one embodiment, an element of the first plurality of RF coil elements is axially offset a threshold amount from a respective element of the second plurality of RF coil elements. For example, an element of the first plurality of RF coil elements can be axially offset 15 degrees, 30 degrees, or another, different number of degrees, from a respective element of the second plurality of RF coil elements. The first plurality and the second plurality can include the same number of RF coil elements, or can include different numbers of RF coil elements. For example, in one embodiment, the first plurality can include eight RF coil elements, while the second plurality can include seven RF coil elements. Other, different numbers of RF coil elements can be employed.

In another embodiment, the RF coil elements of the multi-turn MRI RF coil array can be arranged in a three-row configuration, wherein each row can be as described herein (e.g., in connection with FIGS. 3 and 4). For example, a three-row single layer MRI RF coil array can include a first row that includes at least four RF coil elements, a second row that includes at least four RF coil elements, and a third row that includes at least four RF coil elements. In this embodiment, the first row, second row, and third row can be aligned axially, two of them can be aligned axially with the third unaligned, or all three can be unaligned axially. In another embodiment, other different numbers of rows, number of RF coil elements, or combinations of alignments can be employed.

For example, in one embodiment, MRI RF coil array 520 includes a first plurality of RF coil elements 522, a second plurality of RF coil elements 524, and a third plurality of RF coil elements (not illustrated). In this embodiment, the first plurality of RF coil elements 522, the second plurality of RF coil elements 524, and the third plurality of RF coil elements are radially disposed about a longitudinal axis. The first plurality 522, the second plurality 524, and the third plurality are longitudinally offset a threshold amount along the longitudinal axis. In one embodiment, an element of the first plurality 522 of RF coil elements is axially offset a threshold amount from a respective element of the second plurality 524 of RF coil elements or the third plurality of RF coil elements. The first plurality 522, the second plurality 524, and the third plurality can include the same number of RF coil elements, or can include different numbers of RF coil elements. For example, in one embodiment, the first plurality 522 can include eight RF coil elements, the second plurality 524 can include six RF coil elements, and the third plurality may include seven RF coil elements. In another embodiment, the first plurality 522, the second plurality 524, or the third plurality can include other, different numbers of RF coil elements.

Various embodiments discussed herein provide several advantages over existing systems. A first advantage of embodiments discussed herein is the ability to achieve a higher Q value and a higher unloaded vs loaded Q ratio using a multi-turn coil array at low field (e.g., <1 T). A second advantage of embodiments discussed herein is the ability to provide improved isolation among all channels for multi-turn coils and coil arrays.

Additionally, in such coils and coil arrays, there is always a ring resonant mode due to self-inductance $L_3$. In some coils and coil arrays, this resonant frequency can be very close to the working frequency, which creates a technical difficulty for coil tuning. A third advantage of embodiments discussed herein is that using the multi-turn approach discussed herein can ensure that the ring mode frequency is much higher than the working frequency, because $C_2$ is significantly smaller than for a one turn coil.

Examples herein can include subject matter such as a method, means for performing acts or blocks of the method, at least one machine-readable medium including executable instructions that, when performed by a machine (e.g., MRI machine, for example as described herein, etc.) cause the machine to perform acts of the method or of an apparatus or system according to embodiments and examples described.

A first example embodiment comprises a magnetic resonance imaging (MRI) radio frequency (RF) coil array on a cylindrical former, the MRI RF coil array configured to operate in a transmit (Tx) mode or in a receive (Rx) mode, the MRI RF coil array comprising: At least one row along a cylindrical axis direction, wherein each row of the at least one row comprises more than three and up to eight array coil elements that cover the whole circumference, where each coil element has more than 1 turn, where all coil elements share at least one ring on one side, where neighboring element has overlap and/or shared capacitor to achieve good isolation between neighboring elements, where capacitor on the ring of each coil elements are adjusted to achieve good isolation among non-direct neighbors.

A second example embodiment comprises the first example embodiment, wherein the cylindrical former is for head, knee, leg and wrist anatomies.

The following examples are additional embodiments.

Example 1 is a magnetic resonance imaging (MRI) radio frequency (RF) coil array configured to operate in at least one of a transmit (Tx) mode or a receive (Rx) mode, the MRI RF coil array comprising: four or more RF coil elements arranged to circumferentially enclose a cylindrical axis of a cylindrical former associated with the MRI RF coil array, wherein each RF coil element of the four or more RF coil elements comprises a first capacitor of that RF coil element and a loop of that RF coil element comprising at least two turns; and a ring structure that facilitates decoupling of the four or more RF coil elements, wherein each RF coil element of the four or more RF coil elements is adjacent to two associated neighboring RF coil elements of the four or more RF coil elements and is non-adjacent to one or more other coil elements of the four or more RF coil elements, wherein each RF coil element of the four or more RF coil elements has a shared side of that RF coil element in common with the ring structure, wherein the shared side of that RF coil element comprises a second capacitor of that RF coil element, and wherein, for each RF coil element of the four or more RF coil elements, a capacitance of the second capacitor of that RF coil element is selected to mitigate inductive coupling between that RF coil element and the one or more other RF coil elements to which that RF coil element is non-adjacent.

Example 2 comprises the subject matter of any variation of any of example(s) 1, wherein the four or more RF coil elements comprise at most eight RF coil elements.

Example 3 comprises the subject matter of any variation of any of example(s) 1-2, wherein the cylindrical former is for at least one of a head anatomy, a knee anatomy, a leg anatomy, or a wrist anatomy.

Example 4 comprises the subject matter of any variation of any of example(s) 1-3, wherein each RF coil element of the four or more RF coil elements shares overlap with the two associated neighboring RF coil elements to which that RF coil element is adjacent, wherein the shared overlap mitigates inductive coupling between that RF coil element and the two associated neighboring RF coil elements to which that RF coil element is adjacent.

Example 5 comprises the subject matter of any variation of any of example(s) 1-4, wherein each RF coil element of the four or more RF coil elements comprises a second capacitor shared with one RF coil element of the two associated neighboring RF coil elements to which that RF coil element is adjacent and a third capacitor shared with the other RF coil element of the two associated neighboring RF coil elements to which that RF coil element is adjacent, wherein the second capacitor and the third capacitor mitigate inductive coupling between that RF coil element and the two associated neighboring RF coil elements to which that RF coil element is adjacent.

Example 6 comprises the subject matter of any variation of any of example(s) 1-5, wherein, for each RF coil element, the capacitance of the shared capacitor of that RF coil element is selected to minimize inductive coupling between that RF coil element and the one or more other RF coil elements to which that RF coil element is non-adjacent, based on a total inductance of that RF coil element, a total capacitance of that RF coil element, and a working frequency.

Example 7 is a magnetic resonance imaging (MRI) radio frequency (RF) coil array configured to operate in at least one of a transmit (Tx) mode or a receive (Rx) mode, the MRI RF coil array comprising: one or more rows of RF coil elements, wherein the RF coil elements of each row of RF coil elements are arranged to circumferentially enclose a cylindrical axis of a cylindrical former associated with the MRI RF coil array, wherein each row of the one or more rows comprises: four or more RF coil elements of that row, wherein each RF coil element of the four or more RF coil elements of that row comprises a first capacitor of that RF coil element and a loop of that RF coil element comprising at least two turns; and a ring structure of that row that facilitates decoupling of the four or more RF coil elements of that row, wherein each RF coil element of the four or more RF coil elements of that row is adjacent to two associated neighboring RF coil elements of the four or more RF coil elements of that row and has one or more non-adjacent RF coil elements of the four or more RF coil elements of that row, wherein each RF coil element of the four or more RF coil elements of that row has a shared side of that RF coil element in common with the ring structure of that row, wherein the shared side of that RF coil element comprises a second capacitor of that RF coil element, and wherein, for each RF coil element of the four or more RF coil elements of that row, a capacitance of the second capacitor of that RF coil element is selected to mitigate inductive coupling between that RF coil element and the one or more non-adjacent RF coil elements of the four or more RF coil elements of that row.

Example 8 comprises the subject matter of any variation of any of example(s) 7, wherein, for each row, the four or more RF coil elements of that row comprise at most eight RF coil elements.

Example 9 comprises the subject matter of any variation of any of example(s) 7-8, wherein the cylindrical former is for at least one of a head anatomy, a knee anatomy, a leg anatomy, or a wrist anatomy.

Example 10 comprises the subject matter of any variation of any of example(s) 7-9, wherein, for each row, each RF coil element of the four or more RF coil elements of that row shares overlap with the two associated neighboring RF coil elements of that row to which that RF coil element is adjacent, wherein the shared overlap mitigates inductive coupling between that RF coil element and the two associated neighboring RF coil elements of that row to which that RF coil element is adjacent.

Example 11 comprises the subject matter of any variation of any of example(s) 7-10, wherein, for each row, each RF coil element of the four or more RF coil elements of that row comprises a second capacitor shared with one RF coil element of the two associated neighboring RF coil elements to which that RF coil element is adjacent and a third capacitor shared with the other RF coil element of the two associated neighboring RF coil elements to which that RF coil element is adjacent, wherein the second capacitor and the third capacitor mitigate inductive coupling between that RF coil element and the two associated neighboring RF coil elements to which that RF coil element is adjacent.

Example 12 comprises the subject matter of any variation of any of example(s) 7-11, wherein, for each row, the capacitance of the shared capacitor of each RF coil element of that row is selected to minimize inductive coupling between that RF coil element and the one or more other RF coil elements of that row to which that RF coil element is non-adjacent, based on a total inductance of that RF coil element, a total capacitance of that RF coil element, and a working frequency.

Example 13 comprises the subject matter of any variation of any of example(s) 7-12, wherein the one or more rows comprises at least a first row and a second row that is different from the first row, wherein the first row is longitudinally offset from the second row with respect to the cylindrical axis.

Example 14 comprises the subject matter of any variation of any of example(s) 13, wherein the first row comprises N RF coil elements of the first row and the second row comprises N RF coil elements of the second row, wherein N is at least four.

Example 15 comprises the subject matter of any variation of any of example(s) 14, wherein, for each RF coil element of the first row, a corresponding RF coil element of the N RF coil elements of the second row is azimuthally aligned with that RF coil element with respect to the cylindrical axis.

Example 16 comprises the subject matter of any variation of any of example(s) 14, wherein, for each RF coil element of the first row, a corresponding RF coil element of the N RF coil elements of the second row is azimuthally offset from that RF coil element with respect to the cylindrical axis.

Example 17 comprises the subject matter of any variation of any of example(s) 13-16, wherein the first row comprises M RF coil elements of the first row and the second row comprises N RF coil elements of the second row, wherein both M and N are at least four, and wherein M is different than N.

Example 18 is a magnetic resonance imaging (MRI) apparatus, comprising: a controller; a primary coil connected to the controller; and a magnetic resonance imaging (MRI) radio frequency (RF) coil array configured to operate in at least one of a transmit (Tx) mode or a receive (Rx) mode, the MRI RF coil array comprising: one or more rows of RF coil elements, wherein the RF coil elements of each row of RF coil elements are arranged to circumferentially enclose a cylindrical axis of a cylindrical former associated with the MRI RF coil array, wherein each row of the one or more rows comprises: four or more RF coil elements of that row, wherein each RF coil element of the four or more RF coil elements of that row comprises a first capacitor of that RF coil element and a loop of that RF coil element comprising at least two turns; and a ring structure of that row that facilitates decoupling of the four or more RF coil elements of that row, wherein each RF coil element of the four or more RF coil elements of that row is adjacent to two associated neighboring RF coil elements of the four or more RF coil elements of that row and has one or more non-adjacent RF coil elements of the four or more RF coil elements of that row, wherein each RF coil element of the four or more RF coil elements of that row has a shared side of that RF coil element in common with the ring structure of that row, wherein the shared side of that RF coil element comprises a second capacitor of that RF coil element, and wherein, for each RF coil element of the four or more RF coil elements of that row, a capacitance of the second capacitor of that RF coil element is selected to mitigate inductive coupling between that RF coil element and the one or more non-adjacent RF coil elements of the four or more RF coil elements of that row.

Example 19 comprises the subject matter of any variation of any of example(s) 18, wherein the MRI apparatus is configured to operate at a frequency associated with a $B_0$ field strength of less than 1 T.

Example 20 comprises the subject matter of any variation of any of example(s) 18-19, wherein the cylindrical former is for at least one of a head anatomy, a knee anatomy, a leg anatomy, or a wrist anatomy.

Example 21 is a MRI apparatus comprising a MRI RF coil array according to any variation of any of example(s) 1-20.

Circuits, apparatus, elements, MRI RF coils, arrays, methods, and other embodiments described herein are described with reference to the drawings in which like reference numerals are used to refer to like elements throughout, and where the illustrated structures are not necessarily drawn to scale. Embodiments are to cover all modifications, equivalents, and alternatives falling within the scope of the disclosure and appended claims. In the figures, the thicknesses of lines, layers and/or regions may be exaggerated for clarity. Nothing in this detailed description (or drawings included herewith) is admitted as prior art.

Like numbers refer to like or similar elements throughout the description of the figures. When an element is referred to as being "connected" to another element, it can be directly connected to the other element or intervening elements may be present. In contrast, when an element is referred to as being "directly connected" to another element, there are no intervening elements present. Other words used to describe the relationship between elements should be interpreted in a like fashion (e.g., "between" versus "directly between," "adjacent" versus "directly adjacent," etc.).

In the above description some components may be displayed in multiple figures carrying the same reference signs, but may not be described multiple times in detail. A detailed description of a component may then apply to that component for all its occurrences.

The following includes definitions of selected terms employed herein. The definitions include various examples or forms of components that fall within the scope of a term and that may be used for implementation. The examples are not intended to be limiting. Both singular and plural forms of terms may be within the definitions.

References to "one embodiment", "an embodiment", "various embodiments," "one example", "an example", or "various examples" indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrases "in one embodiment" or "in various embodiments" does not necessarily refer to the same embodiment(s), though it may.

"Circuit", as used herein, includes but is not limited to hardware, firmware, or combinations of each to perform a function(s) or an action(s), or to cause a function or action from another circuit, logic, method, or system. Circuit can include a software controlled microprocessor, a discrete logic (e.g., ASIC), an analog circuit, a digital circuit, a programmed logic device, a memory device containing instructions, and other physical devices. A circuit can include one or more gates, combinations of gates, or other circuit components. Where multiple logical circuits are described, it may be possible to incorporate the multiple logical circuits into one physical circuit. Similarly, where a single logical circuit is described, it may be possible to distribute that single logical logic between multiple physical circuits.

"Computer-readable storage device", as used herein, refers to a device that stores instructions or data. "Computer-readable storage device" does not refer to propagated signals. A computer-readable storage device can take forms, including, but not limited to, non-volatile media, and volatile media. Non-volatile media can include, for example, optical disks, magnetic disks, tapes, and other media. Volatile media can include, for example, semiconductor memories, dynamic memory, and other media. Common forms of a computer-readable storage device can include, but are not limited to, a floppy disk, a flexible disk, a hard disk, a magnetic tape, other magnetic medium, an application specific integrated circuit (ASIC), a compact disk (CD), other optical medium, a random access memory (RAM), a read only memory (ROM), a memory chip or card, a memory stick, and other media from which a computer, a processor or other electronic device can read.

To the extent that the term "includes" or "including" is employed in the detailed description or the claims, it is intended to be inclusive in a manner similar to the term "comprising" as that term is interpreted when employed as a transitional word in a claim.

To the extent that the term "or" is employed in the detailed description or claims (e.g., A or B) it is intended to mean "A or B or both". The term "and/or" is used in the same manner, meaning "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

To the extent that the phrase "one or more of, A, B, and C" is employed herein, (e.g., a data store configured to store one or more of, A, B, and C) it is intended to convey the set of possibilities A, B, C, AB, AC, BC, and/or ABC (e.g., the data store can store only A, only B, only C, A&B, A&C, B&C, and/or A&B&C). It is not intended to require one of A, one of B, and one of C. When the applicants intend to indicate "at least one of A, at least one of B, and at least one of C", then the phrasing "at least one of A, at least one of B, and at least one of C" will be employed.

Although the subject matter has been described in language specific to structural features or methodological acts, it is to be understood that the subject matter defined in the appended claims is not necessarily limited to the specific features or acts described above. Rather, the specific features and acts described above are disclosed as example forms of implementing the claims.

The above description of illustrated embodiments of the subject disclosure, including what is described in the Abstract, is not intended to be exhaustive or to limit the disclosed embodiments to the precise forms disclosed. While specific embodiments and examples are described herein for illustrative purposes, various modifications are possible that are considered within the scope of such embodiments and examples, as those skilled in the relevant art can recognize.

In this regard, while the disclosed subject matter has been described in connection with various embodiments and corresponding Figures, where applicable, it is to be understood that other similar embodiments can be used or modifications and additions can be made to the described embodiments for performing the same, similar, alternative, or substitute function of the disclosed subject matter without deviating therefrom. Therefore, the disclosed subject matter should not be limited to any single embodiment described herein, but rather should be construed in breadth and scope in accordance with the appended claims below.

In particular regard to the various functions performed by the above described components or structures (assemblies, devices, circuits, systems, etc.), the terms (including a reference to a "means") used to describe such components are intended to correspond, unless otherwise indicated, to any component or structure which performs the specified function of the described component (e.g., that is functionally equivalent), even though not structurally equivalent to the disclosed structure which performs the function in the herein illustrated exemplary implementations. In addition, while a particular feature may have been disclosed with respect to only one of several implementations, such feature can be combined with one or more other features of the other implementations as may be desired and advantageous for any given or particular application.

What is claimed is:

1. A magnetic resonance imaging (MRI) radio frequency (RF) coil array configured to operate in at least one of a transmit (Tx) mode or a receive (Rx) mode, the MRI RF coil array comprising:

four or more RF coil elements arranged to circumferentially enclose a cylindrical axis of a cylindrical former associated with the MRI RF coil array, wherein each RF coil element of the four or more RF coil elements comprises a first capacitor and a loop comprising at least two turns; and a ring structure that facilitates decoupling of the four or more RF coil elements, wherein each RF coil element of the four or more RF coil elements is adjacent to two associated neighboring RF coil elements of the four or more RF coil elements and is non-adjacent to one or more other RF coil elements of the four or more RF coil elements, wherein each RF coil element of the four or more RF coil elements has a shared side in common with the ring structure, wherein the shared side of the RF coil element comprises a second capacitor, wherein, for each RF coil element of the four or more RF coil elements, a capacitance of the second capacitor of the RF coil element is selected to mitigate inductive coupling between the RF coil element and the one or more other RF coil elements to which the RF coil element is non-adjacent, and wherein, for each RF coil element of the four or more RF coil elements, a capacitance of the first capacitor of the each RF coil element is a function of the capacitance of the second capacitor of the RF coil element, a resonant frequency of the RF coil element, a total inductance of the RF coil element, and a mutual inductance between the RF coil element and the one or more other RF coil elements of the RF coil element.

2. The MRI RF coil array of claim 1, wherein the cylindrical former is for at least one of a head anatomy, a knee anatomy, a leg anatomy, or a wrist anatomy.

3. The MRI RF coil array of claim 1, wherein each RF coil element of the four or more RF coil elements shares overlap with the two associated neighboring RF coil elements to which the RF coil element is adjacent, and wherein the shared overlap mitigates inductive coupling between the RF coil element and the two associated neighboring RF coil elements to which the RF coil element is adjacent.

4. The MRI RF coil array of claim 1, wherein each RF coil element of the four or more RF coil elements comprises a fourth capacitor shared with one RF coil element of the two associated neighboring RF coil elements to which the RF coil element is adjacent and a third capacitor shared with the other RF coil element of the two associated neighboring RF coil elements to which the RF coil element is adjacent, and wherein the fourth capacitor and the third capacitor mitigate inductive coupling between the RF coil element and the two associated neighboring RF coil elements to which the RF coil element is adjacent.

5. The MRI RF coil array of claim 1, wherein, for each RF coil element, the capacitance of the second capacitor of the RF coil element is selected to minimize inductive coupling between the RF coil element and the one or more other RF coil elements to which the RF coil element is non-adjacent, based on a total inductance of the RF coil element, a total capacitance of the RF coil element, and a working frequency.

6. The MRI RF coil array of claim 1, wherein, for each RF coil element of the four or more RF coil elements, the ring structure has a resonant frequency that is higher than the resonant frequency of the RF coil element.

7. The MRI RF coil array of claim 1, wherein the four or more RF coil elements comprises a first RF coil element and a second RF coil element directly contacting at a first node, wherein the first node is capacitively coupled directly to the ring structure at a second node, and wherein the second node is directly connected to only three capacitors.

8. The MRI RF coil array of claim 7, wherein the four or more RF coil elements consists of eight RF coil elements.

9. A magnetic resonance imaging (MRI) radio frequency (RF) coil array configured to operate in at least one of a transmit (Tx) mode or a receive (Rx) mode, the MRI RF coil array comprising:
one or more rows of RF coil elements, wherein the RF coil elements of each row of RF coil elements are arranged to circumferentially enclose a cylindrical axis of a cylindrical former associated with the MRI RF coil array, wherein each row of the one or more rows comprises:
four or more RF coil elements, wherein each RF coil element of the four or more RF coil elements of the row comprises a first capacitor and a loop comprising at least two turns; and
a ring structure that facilitates decoupling of the four or more RF coil elements of the row,
wherein each RF coil element of the four or more RF coil elements of the row is adjacent to two associated neighboring RF coil elements of the four or more RF coil elements of the row and has one or more non-adjacent RF coil elements of the four or more RF coil elements of the row,
wherein each RF coil element of the four or more RF coil elements of the row has a shared side in common with the ring structure of the row, wherein the shared side of the RF coil element comprises a second capacitor, and
wherein, for each RF coil element of the four or more RF coil elements of the row, a capacitance of the second capacitor of the RF coil element is selected to mitigate inductive coupling between the RF coil element and the one or more non-adjacent RF coil elements of the four or more RF coil elements of the row, and wherein the first and second capacitors of the RF coil element are related by the following equation:

$$C_1 = \frac{C_2}{C_2 w_0^2 (L-M) - 1}$$

where $C_1$ is a capacitance of the first capacitor of the RF coil element, $C_2$ is the capacitance of the second capacitor of the RF coil element, L is an inductance of the loop of the RF coil element, M is a mutual inductance between the RF coil element and the one or more non-adjacent RF coil elements of the RF coil element, and wo is a resonant frequency of the RF coil element.

10. The MRI RF coil array of claim 9, wherein, for row, the four or more RF coil elements of the row comprise at most eight RF coil elements.

11. The MRI RF coil array of claim 9, wherein, for row, each RF coil element of the four or more RF coil elements of the row shares overlap with the two associated neighboring RF coil elements of the row to which the RF coil element is adjacent, and wherein the shared overlap mitigates inductive coupling between the RF coil element and the two associated neighboring RF coil elements of the row to which the RF coil element is adjacent.

12. The MRI RF coil array of claim 9, wherein the one or more rows comprises at least a first row and a second row that is different from the first row, wherein the first row is longitudinally offset from the second row with respect to the cylindrical axis.

13. The MRI RF coil array of claim 12, wherein the first row comprises N RF coil elements of the first row and the second row comprises N RF coil elements of the second row, wherein N is at least four.

14. The MRI RF coil array of claim 13, wherein, for each RF coil element of the first row, a corresponding RF coil element of the N RF coil elements of the second row is azimuthally aligned with the RF coil element with respect to the cylindrical axis.

15. The MRI RF coil array of claim 13, wherein, for each RF coil element of the first row, a corresponding RF coil element of the N RF coil elements of the second row is azimuthally offset from the RF coil element with respect to the cylindrical axis.

16. The MRI RF coil array of claim 12, wherein the first row comprises M RF coil elements of the first row and the second row comprises N RF coil elements of the second row, wherein both M and N are at least four, and wherein M is different than N.

17. The MRI RF coil array of claim 9, wherein, for RF coil element of the four or more RF coil elements of the row, the resonant frequency of the RF coil element is the same as each other RF coil element of the four or more RF coil elements of the row.

* * * * *